(12) United States Patent
Sawaki et al.

(10) Patent No.: US 6,657,097 B1
(45) Date of Patent: Dec. 2, 2003

(54) FLUIDIZED BED REACTOR

(75) Inventors: Itaru Sawaki, Okayama (JP); Kazuhiro Shimizu, Okayama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/520,332

(22) Filed: Mar. 7, 2000

(30) Foreign Application Priority Data

Mar. 8, 1999 (JP) .......................................... P 11-059973

(51) Int. Cl.[7] .............................. C07C 4/00; C07C 2/00; C07C 5/00; C07C 6/00; C07D 307/36
(52) U.S. Cl. ........................ 585/636; 549/262; 585/920; 585/921; 585/924; 585/925
(58) Field of Search ................................ 585/636, 920, 585/921, 924, 925; 549/262

(56) References Cited

FOREIGN PATENT DOCUMENTS

| EP | 0 695 576 | 2/1996 |
|---|---|---|
| WO | WO 88/04199 | 6/1988 |

OTHER PUBLICATIONS

Patent Abstracts of Japan, vol. 014, No. 149 (C–0705), Mar. 22, 1990, JP 02 019370, Jan. 23, 1990.
Daizo Kunii, Fluidization Engineering Second Edition, p. 32, 1991.
W. Volk, et al., Chemical Engineering Progress, vol. 58, No. 3, p. 44–47, "Effect of Reactor Internals on Quality of Fluidization", Mar. 1962.
G. Papa, et al., Chemical Engineering Progress, pp. 32–36, "Optimize Performance of Fluidized–Bed Reactors", Apr. 1995.
J.R. Grace, et al., Chemical and Process Engineering, pp. 127–130, "Design of Fluidised Beds with Internal Baffles", Jun. 1970.

*Primary Examiner*—Shailendra Kumar
*Assistant Examiner*—Elvis O. Price
(74) *Attorney, Agent, or Firm*—Oblon, Spivak, McClelland, Maier & Neustadt, P.C.

(57) ABSTRACT

Disclosed is a fluidized bed reactor wherein the average cross-sectional area occupied by a cooling coil, a dummy pipe and/or a cyclone leg is 10% or more of the average cross-sectional area of said reactor in a dense-phase fluidized catalyst bed region. The fluidized bed reactor in the present invention allows an improved fluidization of catalyst and thus allows an efficient reaction of a hydrocarbon with an oxygen-containing gas in the presence of a catalyst.

5 Claims, 1 Drawing Sheet

——— , ○ : COOLING COIL
——— , ● : DUMMY PIPE

FLUIDIZED BED REACTOR

FIELD OF THE INVENTION

The present invention relates to a fluidized bed reactor and its use. More particularly, the present invention relates to a fluidized bed reactor having improved fluidization and a process for the catalytic oxidation of a hydrocarbon which comprises the reaction of a hydrocarbon with an oxygen containing gas in the presence of a catalyst in the fluidized bed reactor.

BACKGROUND OF THE INVENTION

It is known that a fluidized bed reactor can be widely used for various reactions because of its excellent characteristics. In particular, a fluidized bed reactor makes the best use of a high cooling efficiency and can be operated even in an explosive composition range. For these reasons, the fluidized bed reactor finds a wide application in various oxidation reactions involving oxygen gas, e.g., catalytic oxidation of a hydrocarbon, particularly production of maleic anhydride by the oxidation of a hydrocarbon having four carbon atoms, or production of ethane dichloride by oxy-chlorination of ethylene.

In a fluidized bed reactor, the fluidization of a particulate material in the reactor has a great effect on the results of reaction (The particulate material is normally a catalyst and thus will be simply referred to as "catalyst"). It has been heretofore recognized important to minimize the size of bubbles in a fluidized bed reactor so that the catalyst and the gas can be kept in good contact. To this end, it has been practiced to design the shape of gas distributor so properly that the diameter of bubbles generated can be minimized. It has been also practiced to provide an internal unit in the fluidized bed reactor or raise the superficial gas velocity so that bubble breakage can be accelerated.

Further, JP-W-1-503211 proposes a fluidized bed reactor comprising at least one horizontal cooling coil provided in the interior thereof. It is described that this arrangement provides an improvement in the fluidization of the catalyst and thus allows a proper temperature control. However, this approach leaves something to be desired in the improvement of fluidization.

SUMMARY OF THE INVENTION

The present invention has been worked out for the purpose of providing a fluidized bed reactor which allows the catalyst to be fluidized more uniformly than ever and thus to give an easy control over the reaction.

The inventors made extensive studies of the foregoing problems. As a result, it was found that when the effective cross-sectional area of the dense-phase fluidized bed region of the catalyst in a fluidized bed reactor (region where the catalyst can flow) is within a predetermined range, the fluidization of the catalyst can be remarkably improved and the reaction yield is good. Thus, the present invention has been worked out.

In other words, the first essence of the present invention lies in a fluidized bed reactor comprising a cooling coil, a dummy pipe and/or a cyclone wherein the average cross-sectional area occupied by a cooling coil, a dummy pipe and/or a cyclone leg is 10% or more of the average cross-sectional area of said reactor in a dense-phase fluidized catalyst bed region.

In accordance with preferred embodiments of implication of the present invention, there are provided the foregoing reactor wherein the average cross-sectional area occupied by the cooling coil, dummy pipe and/or cyclone leg is 25% or less of the average cross-sectional area of said reactor in said region; the foregoing reactor wherein the average cross-sectional area occupied by the cooling coil, dummy pipe and/or cyclone leg is from 12 to 20% of the average cross-sectional area of said reactor in said region; the foregoing reactor comprising therein a catalyst containing fine particles having a mass mean particle diameter of from 30 to 100 $\mu$m and a particle diameter of not more than 44 $\mu$m in an amount of from 10 to 80% by weight, preferably from 20 to 70% by weight and having a particle density of not more than 5,000 kg/m$^3$, preferably not more than 4,000 kg/m$^3$; and the foregoing reactor wherein a particulate catalyst is kept fluidized by a gas supplied into the reactor at the lower portion thereof.

The second essence of the present invention lies in a process for the catalytic oxidation of a hydrocarbon which comprises the reaction of a hydrocarbon with an oxygen-containing gas in the presence of a catalyst in the fluidized bed reactor.

In accordance with a preferred embodiment of the present invention, there is provided the foregoing catalytic oxidation process wherein a hydrocarbon having four carbon atoms and a gas containing oxygen are reacted to produce maleic anhydride.

DETAILED DESCRIPTION OF THE INVENTION

Figure 1:
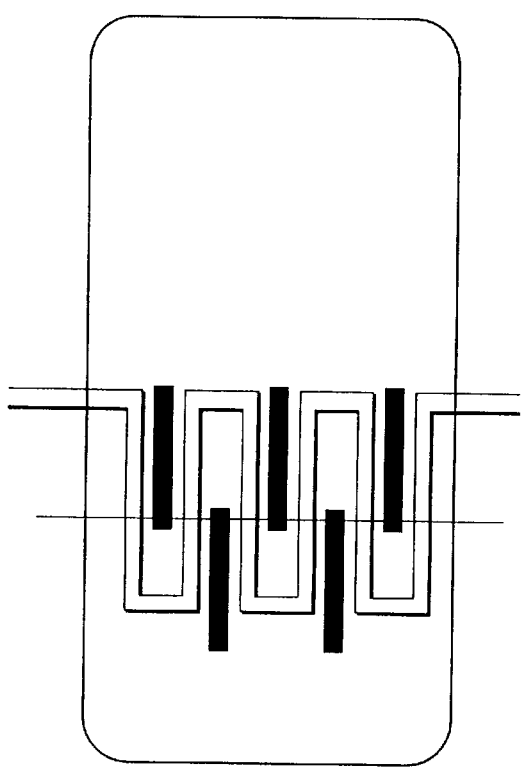
FIG. 1 is a vertical sectional view illustrating a typical example of the fluidized bed reactor according to the present invention.

The present invention will be further described hereinafter.

The fluidized bed reactor according to the present invention is preferably provided with a gas distributor plate defining the lower end of the fluidized bed catalyst, at least one oxygen-containing gas supply pipe, at least one starting material hydrocarbon supply pipe, etc. at the bottom thereof and with at least one product gas outlet at the top thereof. Further, the hydrocarbon inlet is preferably located at a position above the gas distributor plate. Moreover, at least one fine particle collector for separating the product gas and the catalyst entrained by the product gas from the dense-phase fluidized bed from each other may be provided either inside or outside the reactor. Further, the catalyst recovered by the fine particle collector is preferably returned to the lower region of the dense-phase fluidized bed. These gas supply pipes, the gas distributor plate and the fine particle collector provided in the fluidized bed reactor and their position may be as known and usual.

The term "dense-phase fluidized bed region of catalyst" as used in the present invention is meant to indicate the region in the fluidized bed reactor where the fluidized bed catalyst normally dispersed densely, particularly a region having a catalyst fluidized bed density of 300 kg/m$^3$ or more lying above the lowermost end of the cooling coil, dummy pipe and/or cyclone leg. The upper end of the dense-phase fluidized bed region can be known by any commonly used known method. For example, the upper end of the dense-phase fluidized bed region can be known by dividing the differential pressure over a length between the outlet of the ditributor plate and the inlet of the fine particle collector or the product gas outlet from the reactor (differential pressure of fluidized bed) by the differential pressure per unit height of the dense-phase fluidized bed. However, when a horizontal baffle or perforated baffle is provided in the fluidized bed reactor, it is necessary that the differential pressure related thereto be separately measured and then subtracted from the differential pressure of the fluidized bed. More particularly, the range of the dense-phase fluidized bed of the catalyst can be known by measuring the differential pressure over an arbitrary gap (e.g., 0.5 m) from the upper portion of the distributor plate, dividing the differential pressure thus measured by the gap to determine catalyst fluidized bed density, and then confirming the portion where the fluidized bed density is 300 kg/M² or more.

The term "cross-sectional area of the reactor" as used herein is meant to indicate the cross sectional area of the reactor which is calculated on condition that the reactor has no internal units, for example the cooling coil, dummy pipe, cyclone leg, and the like. The cross-sectional area of the reactor is usually calculated by using the inside diameter of the reactor. The term "average cross-sectional area of the reactor" as used herein is meant to indicate the average of said cross-sectional area of the reactor in the foregoing dense-phase fluidized bed region of catalyst.

The method for calculating the average cross-sectional area occupied by the cooling coil, dummy pipe and/or cyclone leg in the foregoing dense-phase fluidized bed region is not specifically limited. Any method can be used so far as it can calculate the quotient obtained by dividing by the height the value obtained by integrating the area occupied by the cooling coil, dummy pipe and/or cyclone leg at a horizontal section in the dense-phase fluidized bed region in the vertical direction. More particularly, the average cross-sectional area can be calculated as follows: In case where the cross-sectional area occupied by the cooling coil, dummy pipe and/or cyclone leg is uniform over a certain range along the vertical length, the cross-sectional area at an arbitrary position in the range may be used as the average cross-sectional area within the range.

The fluidized bed reactor according to the present invention is characterized in that the average cross-sectional area occupied by the cooling coil, dummy pipe and/or cyclone leg in the foregoing dense-phase fluidized catalyst bed region is 10% or more of the average cross-sectional area of the reactor. When the foregoing average cross-sectional area falls below the above defined value, the resulting improvement in fluidization leaves something to be desired. The average cross-sectional area occupied by the cooling coil, dummy pipe and/or cyclone leg is preferably from 10 to 25%, particularly from 12 to 20% of the average cross-sectional area of the reactor. When the average cross-sectional area exceeds 25%, the space for inspecting and maintenance of the cooling coil and cyclone leg cannot be secured or the space becomes too narrow, causing operational problems such as slugging.

As the cooling coil there may be normally used at least one horizontal type or vertical type cooling coil. As the dummy pipe there is preferably used a vertical type dummy pipe in particular. The term "cooling coil" as used herein is meant to indicate at least one equipment provided for allowing a heat transfer medium such as water to flow through the pipe to remove the reaction heat and hence to control the temperature of the reactor. The diameter, length, number and shape of the cooling coil are not specifically limited but may be determined so that the heat transfer area can be secured for the required heat to be removed. The term "dummy pipe" as used herein is meant to indicate a pipe provided as a dummy having no cooling effect when there can be insufficiently secured the required effective cross-sectional area for improving the fluidization of the catalyst by using the cooling coil alone. The shape of the dummy pipe is normally the same as that of the cooling coil but is not specifically limited. For example, it may be in the form of hollow cylinder, U-shaped pipe, polygonal prism pipe, star-shaped prism pipe or cross-shaped prism pipe having two ends closed or in the form of column, U-shaped prism, polygonal prism, star-shaped prism or cross-shaped prism free of hollow portion. The term "cyclone leg" as used herein is meant to generally indicate a facility such as one or a plurality of pipes and nozzles provided to return the substantial portion of the foregoing catalyst recovered from the fine particle collector (e.g., cyclone, filter) for separating the product gas and the catalyst entrained by the product gas from the dense-phase fluidized bed from each other to the lower portion of the fluidized bed reactor. The cyclone leg is preferably opened at the lower region of the dense-phase fluidized bed. Further, the term "horizontal type" or "vertical type" as used herein doesn't indicate a strict expression of angle but indicates a range recognized as almost horizontal or almost vertical.

Figure 2:
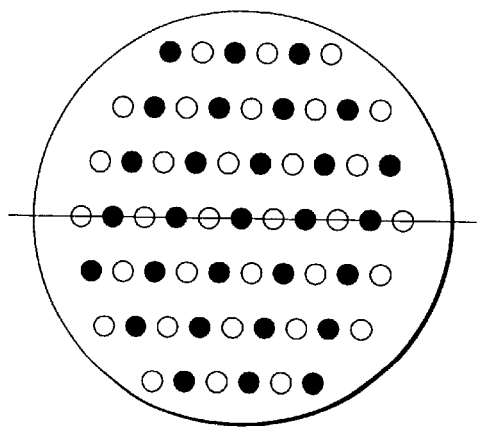
FIG. 2 is a horizontal sectional view illustrating a typical example of the fluidized bed reactor according to the present invention.

As the cooling coil there may be provided either the vertical type cooling coil alone, the horizontal type cooling coil alone or the both types of cooling coils in admixture. The cooling coil to be used herein may be properly selected depending on the size of the reactor, the kind of the reaction, the kind of the catalyst used, etc. The arrangement of the cooling coil, dummy pipe and/or cyclone leg is not specifically limited. However, these units are preferably located uniformly in the dense-phase fluidized bed region so that the effective cross-sectional area can be distributed uniformly as much as possible. A typical embodiment of the fluidized bed reactor according to the present invention is illustrated in FIGS. 1 and 2, but the present invention is not limited thereto.

The fluidized bed reactor of the present invention can be preferably used particularly as a large-sized fluidized bed reactor for the catalytic oxidation reaction of a hydrocarbon on an industrial scale and is suitable for a fluidized bed in gas-solid system for continuously effecting catalytic reaction. The reactor of the present invention allows the catalyst to be fluidized in the fluidized bed effectively for aggregative fluidization of bubbling regime, slug flow regime, turbulent regime, etc. and is a fluidized bed reactor generally called conventional fluidized bed.

As the catalyst to be used in the fluidized bed reactor of the present invention there may be used any catalyst which is used in an ordinary fluidized bed reactor. A catalyst classified as A in Geldert's particle classification map (see Geldert, D., *Powder Technology*, 7, 285 (1973)) containing fine particles having a mass mean particle diameter of from 30 to 100 $\mu$m, preferably from 40 to 80 $\mu$m. and a particle diameter of not more than 44 $\mu$m in an amount of from 10 to 80% by weight, preferably from 20 to 70% by weight and having a particle density of not more than 5,000 kg/m³, preferably not more than 4,000 kg/m³ is preferred. When the mass mean particle diameter falls below 30 $\mu$m or when fine particles having a particle diameter of not more than 44 $\mu$m are present in an amount of more than 80% by weight, the amount of catalyst entrained from the fluidized bed reactor is raised, giving a poor economy. On the contrary, when the mass mean particle diameter exceeds 100 $\mu$m, when fine particles having a particle diameter of not more than 44 μm are present in an amount of less than 10% by weight or when the particle density exceeds 5,000 kg/M³, the particulate material is too heavy and thus is unsuitable for use in fluidized bed reactor. Further, even if the dummy pipe or the like is provided in the fluidized bed reactor as in the present invention, it is difficult to sufficiently exert an effect of improving fluidization.

The fluidized bed reactor according to the present invention can be used in the production of various organic compounds by the catalytic oxidation of a hydrocarbon involving the reaction of a hydrocarbon with a gas containing oxygen in the presence of a catalyst.

In case where a hydrocarbon and an oxygen-containing gas are reacted in the presence of a catalyst in the fluidized bed reactor according to the present invention, the catalyst on the gas distributor plate is fluidized by the gas supplied into the reactor at the lower portion thereof. A dense-phase fluidized bed is then formed above the gas distributor plate. Catalytic oxidation reaction takes place in the dense-phase fluidized bed.

Examples of the catalytic oxidation reaction include oxidation reactions such as production of maleic anhydride by oxidation reaction of butane, butene, butadiene or benzene, production of phthalic anhydride by oxidation reaction of orthoxylene or naphthalene and production of ethane dichloride by oxy-chlorination of ethylene.

Thus, another embodiment of the present invention provides a process for the catalytic oxidation of a hydrocarbon involving the reaction of a hydrocarbon with an oxygen-containing gas in the foregoing fluidized bed reactor. The foregoing oxidation reaction itself is a known process which is ordinarily practiced and thus can be efficiently practiced using the reactor of the present invention.

The catalytic oxidation process of the invention is particularly suitable for the production of maleic anhydride by reacting a hydrocarbon having four carbon atoms such as butane, butene or butadiene with an oxygen-containing gas in the presence of a catalyst.

As the catalyst to be used in the reaction there is preferably used one comprising as an active component a mixed oxide made of vanadium and phosphorus as main constituent elements. Such catalyst itself is a known compound which is ordinarily used and can be produced, e.g., by the method described in U.S. Pat. No. 4,525,471, 4,317,778, 4,511,670, 4,520,127, 5,530,144 or 5,498,731. The particle diameter of the catalyst is preferably as defined above.

As the starting material hydrocarbon, butane is particularly preferred. As the oxygen-containing gas there may be normally used air. Alternatively, air diluted with an inert gas or air enriched with oxygen may be used.

The reaction temperature depends on the performance and properties of the catalyst used, contact time, etc. and thus may be properly predetermined. The temperature of the dense-phase fluidized bed is normally from 330° C. to 500° C., preferably from 360° C. to 460° C.

In the foregoing process for the production of maleic anhydride using the fluidized bed reactor, the vanadium-phosphorus-based mixed oxide catalyst on the gas distributor plate is fluidized by the gas supplied into the reactor at the lower portion thereof to form a dense-phase fluidized bed above the gas distributor plate. The oxygen-containing gas, starting material hydrocarbon, etc. may be separately or concurrently supplied into the reactor. The heat generated by the reaction is removed by the horizontal type cooling coil and/or the vertical type cooling coil provided in the dense-phase fluidized bed to control the reaction temperature. In the dense-phase fluidized bed, the starting material hydrocarbon undergoes catalytic oxidation in gas phase to produce maleic anhydride.

The reaction product gas thus obtained contains maleic anhydride as a desired material as well as unreacted oxygen and starting material hydrocarbon, and carbon dioxide, water and carbon monoxide as by-products in various concentrations. The reaction product gas is discharged from the dense-phase fluidized bed while entraining the catalyst, and then introduced into the fine particle collector provided inside or outside the reactor where it is then separated from the entrained catalyst before being withdrawn. The catalyst separated in the fine particle collector is then returned to the dense-phase fluidized bed. Maleic anhydride is recovered from the reaction product gas from which the catalyst has been separated. The recovery of maleic anhydride can be easily accomplished by a method which itself is known and commonly used, e.g., method which comprises absorbing the reaction product gas by an aqueous or organic solvent, and then subjecting the gas-absorbed solution to concentration or distillation.

In general, the superficial gas velocity in the dense-phase fluidized bed in the foregoing reaction is preferably kept at a range of from 0.35 to 0.8 m/sec.

The process according to the invention can be employed when the fluidized bed reactor is newly provided. Alternatively, the dummy pipe or the like can be provided in the existing fluidized bed reactor to improve fluidization.

The present invention will be further described in the following Comparative Example and Exmaple, but the present invention is not limited thereto.

COMPARATIVE EXAMPLE 1

Using a fluidized bed reactor having a cross-sectional area of the reactor about 26 m² provided with vertical type cooling coils and vertical type dummy pipes having the same outer diameter as that of the vertical type cooling coils, maleic anhydride was produced from a butane-containing gas. The reactor was loaded with 59×10³ kg of a vanadium-phosphorus-based mixed oxide catalyst containing fine particles having a mass mean particle diameter of 60 μm and a particle diameter of not more than 44 μm in an amount of 16% by weight and having a particle density of 3,000 kg/m³. Into the reactor were supplied air from a gas supply pipe and a butane-containing gas from a hydrocarbon supply pipe at a constant flow rate of about 55,000 Nm³/hr in all. The cross-sectional area occupied by the cooling coils, dummy pipes and cyclone legs in the dense-phase fluidized catalyst bed region was in the range of from 2.3 to 14.8% of the cross-sectional area of the reactor. The average cross-sectional area occupied by the cooling coils, dummy pipes and cyclone legs in said region was 9.5% of the average cross-sectional area of the reactor. The average cross-sectional area occupied by the cooling coils, dummy pipes and cyclone leg was calculated by summing up the volume occupied by the cooling coil, dummy pipe and cyclone leg every range recognized as being uniform in the cross-sectional area, and then dividing the sum by the height of the dense-phase fluidized catalyst bed region. The height of the dense-phase fluidized bed, the catalyst fluidized bed density, the amount of catalyst and the superficial gas velocity (LV) during the reaction and the yield of maleic anhydride are set forth in Table 1.

EXAMPLE 1

Maleic anhydride was produced in the same manner as in Comparative Example 1 except that vertical type dummy pipes having the same outer diameter as that of the cooling coils were additionally provided uniformly as much as possible such that the cross-sectional area occupied by the cooling coils, dummy pipes and cyclone legs in the dense-phase fluidized catalyst bed region was in the range of from 2.3 to 17.8% of the cross-sectional area of the reactor and the average cross-sectional area occupied by the cooling coils, dummy pipes and cyclone legs in said region was 14.7% of the average cross-sectional area of the reactor. The bed height of the dense-phase fluidized bed, the catalyst fluidized bed density, the amount of catalyst and the superficial gas velocity (LV) during the reaction and the yield of maleic anhydride are set forth in Table 1.

TABLE 1

|  | Comparative Example 1 | Example 1 |
|---|---|---|
| Bed height of dense-phase fluidized catalyst bed (m) | 4.4 | 4.7 |
| Catalyst fluidized bed density (kg/m$^3$) | 570 | 550 |
| Amount of catalyst (kg) | 59 × 10$^3$ | 59 × 10$^3$ |
| LV (m/sec) | 0.63 | 0.53 |
| Yield of maleic anhydride (%) | 49 | 50 |

As can be seen in Table 1, when the fluidized bed reactor according to the present invention is used, the resulting catalyst bed has a raised bed height despite the low LV and the catalyst fluidized bed density is lowered for the same amount of catalyst, demonstrating that the fluidization of catalyst is improved. Further, the yield of maleic anhydride is enhanced.

In accordance with the present invention, a fluidized bed reactor allowing improved fluidization of catalyst can be provided. The foregoing fluidized bed reactor allows efficient reaction of a hydrocarbon with an oxygen-containing gas in the presence of a catalyst and thus is very useful on an industrial basis.

What is claimed is:

1. A process for catalytic oxidation of a hydrocarbon, which comprises reacting a hydrocarbon with an oxygen containing gas in the presence of a catalyst in a fluidized bed reactor, the average cross-sectional area occupied by a cooling coil, a dummy pipe and/or a cyclone leg is 10% or more of the average cross-sectional area of said reactor in a dense-phase fluidized catalyst bed region.

2. The process according to claim 1, wherein the reactor comprises an average cross-sectional area occupied by the cooling coil, dummy pipe and/or cyclone leg is 25% or less of the average cross-sectional area of said reactor in said region.

3. The process according to claim 1, wherein the reactor comprises an average cross-sectional area occupied by the cooling coil, dummy pipe and/or cyclone leg is from 12 to 20% of the average cross-sectional area of said reactor in said region.

4. The process according to claim 1, wherein the reactor comprises a catalyst containing fine particles having a mass mean particle diameter of from 30 to 100 μm and a particle diameter of not more than 44 μm in an amount of from 10 to 80% by weight and having a particle density of not more than 5,000 kg/m$^3$.

5. The process according to claim 1, further comprising recovering maleic anhydride.

* * * * *